Figure 1:
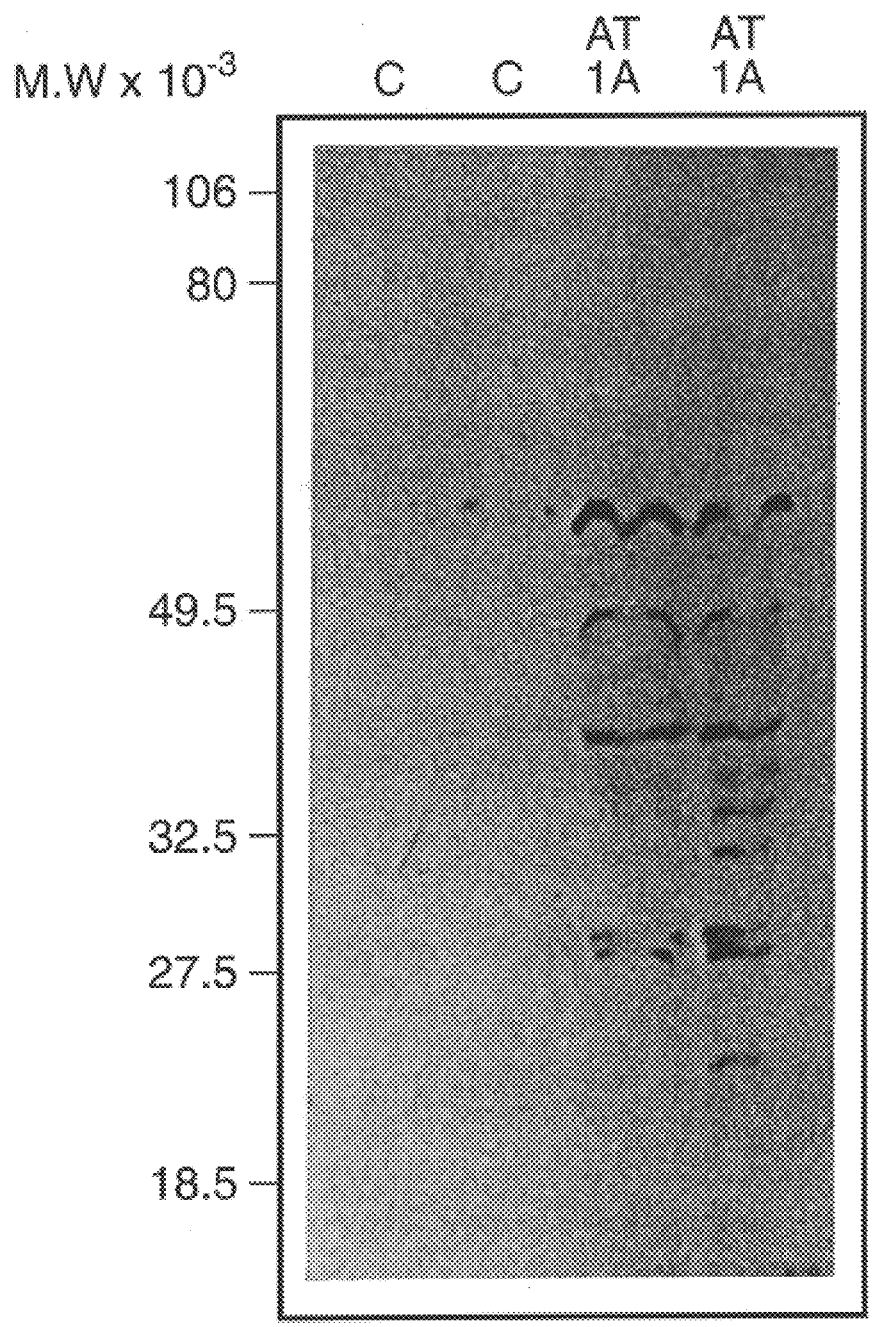

United States Patent [19]
Vinson et al.

[11] Patent Number: 6,063,620
[45] Date of Patent: *May 16, 2000

[54] TYPE I ANGIOTENSIN II RECEPTOR SPECIFIC MONOCLONAL ANTIBODIES AND HYBRIDOMAS

[75] Inventors: Gavin Paul Vinson; Stewart Barker, both of London, United Kingdom

[73] Assignee: Queen Mary & Westfield College, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/624,374
[22] PCT Filed: Sep. 27, 1994
[86] PCT No.: PCT/GB94/02100
§ 371 Date: Mar. 27, 1996
§ 102(e) Date: Mar. 27, 1996
[87] PCT Pub. No.: WO95/09186
PCT Pub. Date: Apr. 6, 1995

[30] Foreign Application Priority Data

Sep. 27, 1993 [GB] United Kingdom .................... 9319877

[51] Int. Cl.[7] .............................. C12N 15/85; C12N 5/12; C07K 16/00
[52] U.S. Cl. ........................... 435/326; 435/331; 435/334; 435/346; 530/388.2; 530/399; 530/391.1; 530/391.3
[58] Field of Search ............................... 530/388.22, 399, 530/391.1, 391.3; 435/346, 331, 334

[56] References Cited

PUBLICATIONS

Eshhar et al (1985) Monoclonal Antibody Strategy and Techniques in Hybridoma Technology in the Biosciences & Medicine. Ed Timothy Springer pp. 3–25.

Zelezna et al Biochemical and Biophys. Research Comm. vol. 183, No. 2 (1992) pp. 781–788. (Submitted by Applicant).

*Primary Examiner*—Paula K. Hutzell
*Assistant Examiner*—Geetha P. Bansal
*Attorney, Agent, or Firm*—Fay, Sharpe, Fagan, Minnich & McKee, LLP

[57] ABSTRACT

The present invention relates to a novel hybridoma cell line which secretes monoclonal antibodies capable of binding to the $AT_1$ subtype of the Angiotensin II receptor. It also relates to monoclonal antibodies secreted by the hybridoma, which antibodies may be used in diagnostic test kits as well as having therapeutic applications.

11 Claims, 4 Drawing Sheets

Immunoblot of solubilised membrane proteins from control COS-7 cells (C), and COS-7 cells expressing rat adrenal $AT_{1A}$ receptors using anti- $AT_1$ monoclonal antibody produced by hybridoma cell line No. 930720117

SEQUENCE LISTING (1) GENERAL INFORMATION:

(iii) NUMBER OF SEQUENCES: 1

```
(2) INFORMATION FOR SEQ ID NO:1:

(i) SEQUENCE CHARACTERISTICS:
        (A) LENGTH:      10
        (B) TYPE: amino acid
        (C) STRANDEDNESS:  unknown
        (D) TOPOLOGY:  linear (ii) MOLECULE TYPE:  peptide (vi) ORIGINAL SOURCE:
         (H) CELL LINE:  Hybridoma (xi) SEQUENCE DESCRIPTION:  SEQ ID NO:1:

Glu Asp Gly Ile Lys Arg Ile Gln Asp Asp
1               5                   10
```

TYPE I ANGIOTENSIN II RECEPTOR SPECIFIC MONOCLONAL ANTIBODIES AND HYBRIDOMAS

The present invention relates to a novel hybridoma cell line, in particular it relates to a novel hybridoma cell line which secretes monoclonal antibodies capable of binding to the $AT_1$ subtype of the Angiotensin II receptor ($AT_1$ receptor). The invention also relates to monoclonal antibodies secreted by the hybridoma, which antibodies may be used in a test kit having several diagnostic and monitoring applications. It also relates to the use of the monoclonal antibodies in therapeutic applications such as the control of smooth muscle stimulation.

The hormone angiotensin II (Ang II) forms part of the renin—angiotensin system which helps to control electrolyte balance and blood pressure within the body. There are several tissues within the body upon which Ang II acts, they include the adrenal gland, uterus, liver, brain and kidney.

Amongst the several established functions of angiotensin II, it is known to stimulate smooth (unstriated) muscle cell contraction. It stimulates the contraction of smooth muscle cells in the blood vessel wall thus causing vaso-constriction, which leads to hypertension. Most treatments for high blood pressure will include blockage of angiotensin function in one way or another. Smooth muscle also occurs in other locations, for example in the uterus and in the gastrointestinal tract, and elsewhere.

Ang II also stimulates the secretion of aldosterone by the adrenal cortex. Aldosterone is a potent hormone which acts primarily on the kidney to promote sodium retention and thus inter alia, heightens the hypertensive effects of angiotensin acting directly on the vasculature.

Ang II is known to act on various sites in the brain, and one of its actions in animals is the regulation of thirst and drinking.

Angiotensin also has trophic effects on the vasculature, promoting growth of the muscles in the arterial wall. It is also thought to be angiogenic, i.e. it causes vascularisation of newly developing tissue.

The actions of angiotensin II in cells are mediated through two important intracellular signalling mechanisms. When the hormone binds to its receptor, it activates a specific enzyme, phospholipase C, which acts upon a constituent of the cell membrane called phosphatidyl inositol. This is split by the enzyme into two moieties, called inositol trisphosphate (IP3), and diacylglycerol (DAG). Both of these are involved in eliciting further effects within the target cell. IP3 stimulates increased cellular cytosolic calcium concentrations, which in turn evokes other cellular responses, whereas DAG stimulates another specific enzyme called protein kinase C (PKC).

Most of the established effects of Ang II have been found to occur via the $AT_1$ subtype of the Ang II receptor, which is a seven transmembrane domain receptor. This receptor has been cloned and sequenced from a variety of tissues, and has been found to be a 359 amino acid polypeptide with a predicted molecular weight of around 40 kD (Bernstein and Alexander, (1992), *Endocr. Rev.*, 13, 381–386). Studies using photo-affinity labelling and crosslinking agents have suggested molecular weights for mature receptor of approximately 65 kD and 116 kD, respectively, which may reflect glycosylation of asparagine residues within the extracellular domain.

Whilst polyclonal antibodies and anti-idiotypic antibodies have been prepared to the Ang II receptor, from which it has been postulated that the receptor has a molecular weight of from 60 to 95 kD, and 63 kD respectively, to date no-one has succeeded in preparing a monoclonal antibody to this receptor.

Garcia et al in *Science*, 257, 502–507, (1992) described the preparation of a monoclonal antibody to the hormone Ang II itself.

Couraud in *J. Immunol.*, 138 (4), 1164–8, (1987) described the preparation of anti-idiotypic serum from a rabbit immunized with one anti-angiotensin II monoclonal antibody. Pfister et al in *Regul. Pept.*, 44 (2), 109–17, (1993) described the preparation of anti-idiotypic antibody that bound to the angiotensin II receptor. The preparation of polyclonal antibodies to the $AT_1$ subtype of the angiotensin II receptor was described by Zelezna et al in *Biochem & Biophys. Res. Comm.*, 183 (2), 781–788, (1992), and Paxton et al in *Hypertension*, 21 (6), 1062–1065, (1993). Phillips et al in *Am. J. Physiol.*, 264 (6) 989–95, (1993) described the preparation of polyclonal antibodies to amino acids 225–257 of the $AT_1$ receptor protein, whereas Richards et al, in *Hypertension*, 21 (6), 1062–1065, (1993) merely mentioned anti serum raised against amino acids 14–23 of the rat vascular $AT_1$ receptor sequence, with no mention of the preparation of monoclonal antibodies.

It has now been found that by immunising mice with a synthetic peptide corresponding to amino acid residues 8–17 of the rat vascular smooth muscle $AT_1$ receptor (Murphy, T. J. et al, (1992), *Nature*, 351, 233–236), and thereafter fusing spleen cells from the immunised mice with mouse myeloma cells, a novel hybridoma cell line is produced, which secretes monoclonal antibodies to the $AT_1$ subtype of the Ang II receptor.

According to one aspect of the invention there is provided a hybridoma cell line which produces monoclonal antibodies capable of binding to the $AT_1$ subtype of the angiotensin II receptor. A hybridoma cell line that secretes such monoclonal antibodies was deposited on Jul. 22, 1993 with the European Collection of Animal Cell Cultures, Porton Down, United Kingdom, under the Budapest Treaty, and designated accession No. 93072117.

Such a hybridoma cell line produces antibodies which bind specifically to amino acid residues 8 to 17 of the rat vascular smooth muscle $AT_1$ receptor. It was found, however, that the monoclonal antibodies would bind to the $AT_1$ receptor in bovine and human tissue, as well as in rat tissue. To date this sequence of amino acid residues has been found, and is therefore conserved, in all mammalian $AT_1$ receptors so far cloned. Thus the hybridoma cell line produces antibodies that bind specifically to a peptide having the following amino acid sequence (SEQ. ID. NO.1):

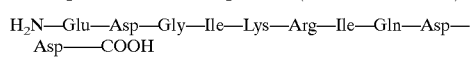

According to a second aspect of the invention there is provided a monoclonal antibody that binds to the $AT_1$ subtype of the angiotensin II receptor. Such monoclonal antibodies bind specifically to amino acid residues 8–17 of the mammalian $AT_1$ receptor, that is they bind specifically to a peptide having the amino acid sequence given above.

A hybridoma cell line, according to the invention, can be prepared by immunising inbred mice by techniques well known in the art (Kohler and Milstein, (1975), *Nature*, 256, 495–497). A peptide was synthesised which corresponds to amino acid residues 8–17 (extracellular) of the published rat vascular smooth muscle $AT_1$ receptor. The peptide was then conjugated to bovine serum albumin (BSA) and used to immunise mice.

Following a booster injection of the peptide-BSA conjugate the mouse spleens were removed, and the spleenocytes were combined with mouse myeloma cells. Mixed myeloma—lymphocyte hybrids were selected by growth in hypoxanthine, thymidine and aminopterin in an appropriate cell culture medium.

The presence of hybridoma cell lines producing monoclonal antibodies to the $AT_1$ subtype of the angiotensin II receptor was first detected by screening the hybridoma conditioned medium for binding to a rat liver cell suspension. Such positive binding was detected using peroxidase—conjugated rabbit anti-mouse immunoglobulin (IgG) antibody. Following the initial screening, cell cultures showing positive results were expanded and tested for specific binding to rat adrenal glomerulosa on both frozen sections and dispersed cell smears, using a fluorescein-conjugated rabbit anti-mouse (IgG) antibody. The integrity of the anti-$AT_1$ receptor monoclonal antibodies produced by the hybridoma was confirmed by binding to rat $AT_{1A}$ receptor transiently expressed by transfected Cos-7 cells.

The monoclonal antibodies of the present invention may be tagged with compounds that fluoresce at various wavelengths, so that the location and distribution of $AT_1$ receptors in body tissues can be determined by immunohistological techniques. For example, using this monoclonal antibody $AT_1$ receptors have been found in breast tumours, thus the antibody may be useful in the cancer diagnostic field.

In addition, using the monoclonal antibody of the present invention a hitherto unknown site of action for Ang II has been discovered. It has been found that both rat and human sperm tails express the angiotensin II receptor, and the physiology of the regulation of its expression leads to the possibility that the hormone may be profoundly important in the control of sperm motility, with a potential effect on male fertility. The monoclonal antibodies of the present invention may thus be used in a standard radioimmuno-assay or enzyme-linked immunosorbant assay to study, and possibly measure, sperm motility, as well having a use in contraception.

According to a further aspect of the invention there is provided a diagnostic test kit comprising the monoclonal antibodies of the present invention attached to a detectable label. Such detectable labels include radioisotopes, enzymes and fluorescent compounds.

It has been found that addition of the monoclonal antibodies according to the present invention to living cells inhibits the angiotensin II-generated IP3 response, but it has no action on PKC activation. Thus the antibody interacts highly specifically with just one of the two major signalling pathways stimulated by angiotensin II. This property can be used experimentally to discriminate between the effects of these two pathways, as well as in therapeutic applications. For example, the monoclonal antibodies may be used in controlling vaso-constriction and therefore used to treat hypertension, as well as for the regulation of menstruation and the control of uterine contractions to prevent miscarriage.

Furthermore these monoclonal antibodies can be used in both immunohistochemistry and immunoelectronmiscroscopy, and may have applications in immunoblotting and immunocytological staining.

The invention is illustrated by the following example.

EXAMPLE 1

Peptide Synthesis

A peptide was synthesised corresponding to amino acid residues 8–17 (extracellular) of the published rat vascular smooth muscle $AT_1$ receptor, with the addition of a cysteine residue to facilitate subsequent conjugation to bovine serum albumin (BSA) at either the carboxy-terminal end or the amino terminal end respectively, via an N-Succinimidyl 3-(2-pyridyldithio) proprionate (SPDP) bridge. The synthesis was carried out using FMOC chemistry on an automated synthesiser, followed by reverse phase HPLC. FMOC chemistry is the use of fluorenylmethoxy carbonyl protected amino acids in peptide synthesis.

Immunogen Preparation and Immunisation

To prepare the peptide-BSA conjugates, a 0.22 mM solution of BSA, in degassed 100 mM sodium phosphate buffer containing 100 mM sodium chloride (SPSC buffer; pH 7.5), was 'activated' by incubation for 60 min at room temperature with 20 mM SPDP (in absolute ethanol) at a ratio of 9:1 (v/v) followed by dialysis in SPSC buffer. 3 mg of peptide in 1.2 ml SPSC buffer was then incubated with 6 ml of 'activated' BSA for 60 min at room temperature, followed by further dialysis in SPSC buffer. Balb C/c mice (8 weeks old) were then immunised by subcutaneous injection with 0.2 ml of a 1:1 emulsion of peptide-BSA conjugate in SPSC buffer (representing approximately 400 μg/ml peptide) and Freund's complete adjuvant. This was followed by a booster injection four weeks later using a similar emulsion of peptide conjugate in Freund's Incomplete adjuvant. Four days later the mouse spleens were removed.

Production of Hybridomas

Sp2/0-Ag-14 mouse myeloma cells were cultured in RPMI 1640 medium supplemented with 20% (v/v) fetal bovine serum (FBS). These myeloma cells were combined with spleen cells obtained from the immunised mice, and the formation of fused hybrids was aided using 40% (v/v) polyethylene glycol. Mixed myeloma-lymphocyte hybrids were selected by culture in 96-well plates using RPMI containing 20% FBS and hypoxanthine (13.6 mg/l), aminopterin (0.19 mg/l) and thymidine (3.88 mg/l) (HAT) (Galfre and Milstein, (1981), *Methods Enzymol.*, 73, 3–46).

After 14 days of HAT selection, hybridoma conditioned medium was removed and screened for binding to a rat liver cell suspension, which had been washed thoroughly with serum-free medium and fixed, using 3.7% (v/v) formaldehyde in 10 mM phosphate buffered saline (PBS; pH 7.3), on to poly-L-lysine coated 96-well plates. A peroxidase-conjugated rabbit anti-mouse immunoglobin (IgG) antibody was used to detect positive binding, and this was visualised, as a brown colouration, with diaminobenzidine (DAB) reagent containing imidazole. After initial screening, cells from positive wells were expanded into 24-well plates and cultured in RPMI 1640 containing 20% Myoclone (obtained from Gibco BRL, Uxbridge, UK), and hypoxanthine (13.6 mg/l) and thymidine (0.19 mg/l), supplemented with 10% v/v thymocyte conditioned medium. Conditioned media from expanded cultures were then tested for specific binding to rat adrenal glomerulosa on both frozen sections and dispersed cell smears, using a fluorescein-conjugated rabbit anti-mouse IgG as described by Laird, S. M, et al in *Acta Endocrinologica* (Copenh.) (1988) 19, 420–426. Glomerulosa specific populations were then cloned by limiting dilution as described by Goding, J. W. in *J. Immunol. Methods*, (1980), 39, 285–306.

Transfected $AT_1$ Receptor Preparation

Rat $AT_{1A}$ receptors were transiently expressed in COS-7 cells as described by Barker, S., et al in *Biochem Biophys. Res. Commun.*, (1993), 192, 392–398. Cells were sonicated, on ice, in 50 mM Tris-HC buffer (pH 7.4) containing aprotinin (1 μg/ml), soybean trypsin inhibitor (1 μg/ml), phenyl methyl sulfonyl fluoride (30 μg/ml and ethylene diamine tetra-acetic acid EDTA (300 μg/ml), and centrifuged at 800 g for 5 min at 4° C. The resultant supernatant was centrifuged at 100 000 g for 1 hour at 4° C. The particulate fraction was then resuspended in the above buffer and diluted to give 100 μg protein/25 μl. The *Screening and Cloning* preparation was then incubated for 30 min at 4° C. in the presence of 1% (v/v) Triton x100 (Trade Mark) to solubilise membrane proteins. Sham-transfected COS-7 cells were treated similarly.

Gel Electrophoresis and Immunoblotting

100 μg of solubilised proteins, obtained from the membrane fraction of COS-7 cells, prepared as described above, was loaded in each well and proteins were separated by sodium dodecyl sulphate-polyacrylamide gel electrophoresis (SDS-PAGE) on an 8% gel, running at 200 v for approximately 4 hours. Molecular weight markers (106 kD-18.5 kD) were also loaded. Proteins were then electro transferred to Hybond-Enhanced chemiluminescence (ECL) nitrocellulose membranes overnight at 200 mA. The membranes were blocked using PBS containaing 10% (w/v) milk protein for 1 hour at room temperature. After washing thoroughly with PBS containing 0.1% (v/v) Tween 20 (Trade Mark) (PBS-T), membranes were incubated with primary antibody (1:20 v/v in PBS-T) for 1 hour at room temperature. Membranes were washed with PBS-T as before, and then incubated for a further hour at room temperature with horseradish peroxidase-linked sheep anti-mouse Ig antibody, at a dilution of 1:5000 in PBS-T. Following further thorough washing with PBS-T, membranes were treated with ECL reagent and chemiluminescence was detected by exposure to Hyperfilm-ECL.

Results

Amongst the hybridoma clones of interest was one which secreted antibody, and which has been deposited as cell line accession No. 930720117 with the European Collection of Animal Cell Cultrues, Porton Down, UK. To confirm that this cell line truly produced antibody that recognised $AT_1$ receptor, SDS-PAGE and immunoblotting of solubilised proteins obtained from the membrane fraction of COS-7 cells transfected with rat adrenal $AT_{1A}$ receptor cDNA were carried out as described above. FIG. 1 shows that the antibody produced by this cell line identified two prominent protein species with approximate molecular weights of 40 and 60 kG. These were not detected in parallel samples from sham-transfected COS-7 cell controls.

EXAMPLE 2

Use of Monoclonal Antibodies to Control Sperm Motility

Human sperm samples were obtained from 12 volunteers and patients attending the Newham Hospital assisted fertility clinic. Samples were suspended in modified minimum essential medium with Earle's salts (MEM) and glutamine and viewed in a Makler chamber using an Olympus inverted microscope fitted with an Olympus ARTF-2 video camera. Fields were recorded on video tape and percentage motility evaluated.

Percentage motility was estimated on playback of the video tapes by freezing the frame to count all of the sperm within a field and then, in forward mode, by counting immotile sperm, i.e. those which within the period of observation did not move to an adjacent square (100 μmeter) on the Makler Chamber grid. In practice, rigid use of this definition was rarely necessary as sperm were either completely immotile or progressed freely.

One series of samples was kept as controls. To a second series Angiotensin II amide (10 nmole/1)was added. A third series was treated with monoclonal antibody to the $AT_1$ receptor before angiotensin was added.

Velocity was measured by timing forwardly progressive sperm traversing the grid on the Makler Chamber and timing them manually.

Figure 2A:
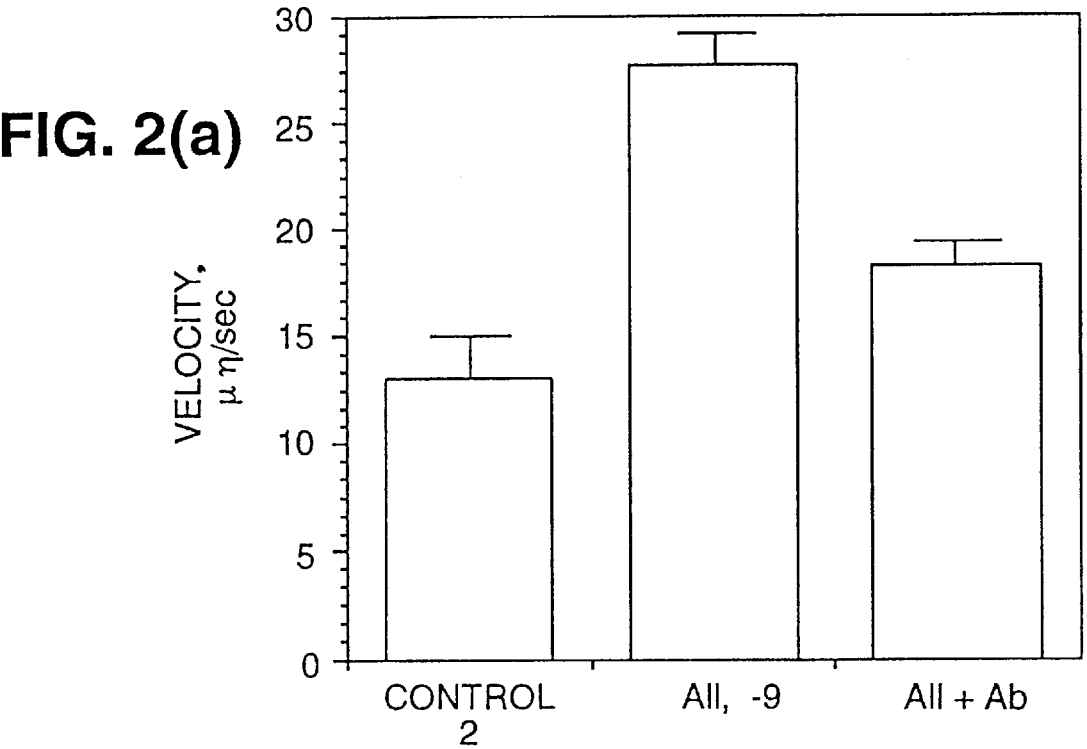
Figure 2B:
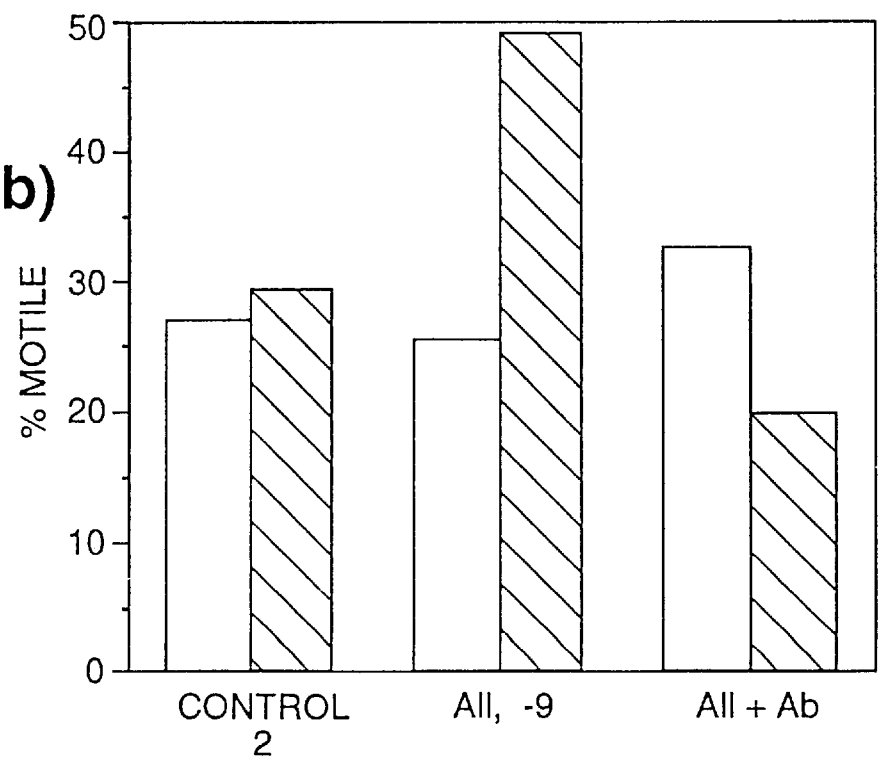
Figure 3A:
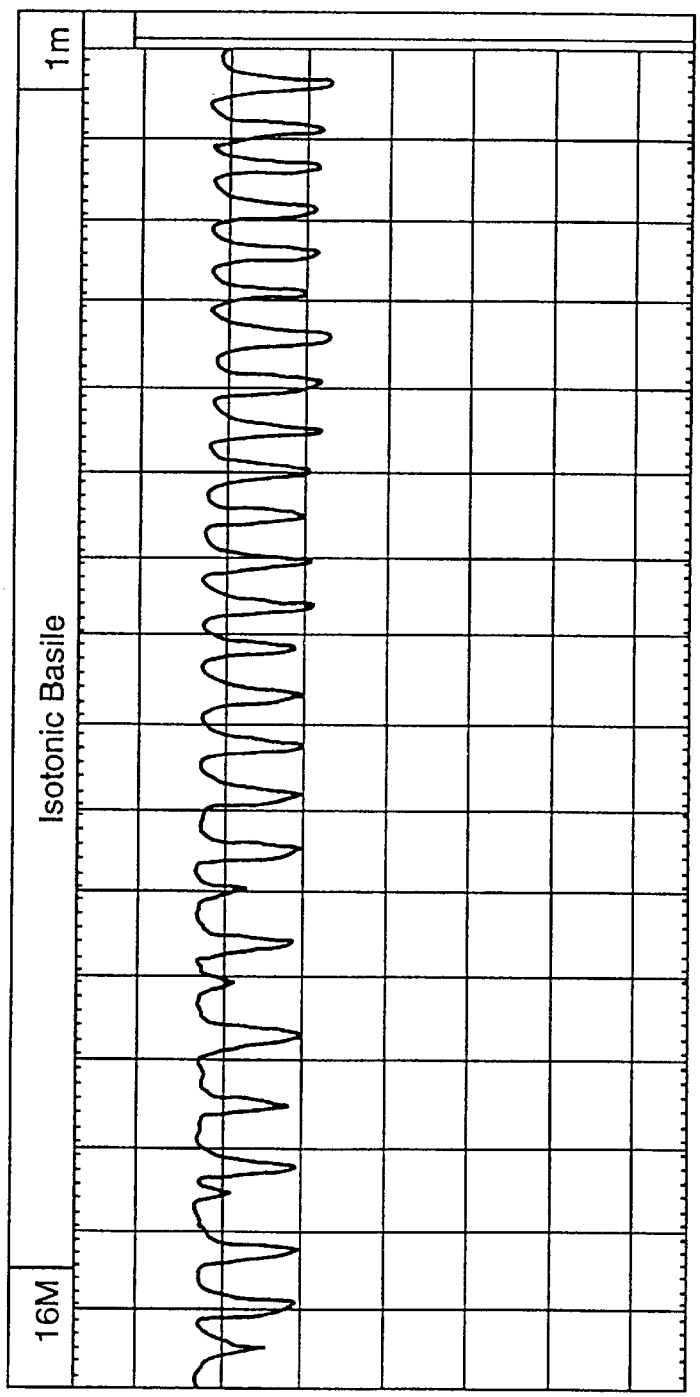
Figure 3A:
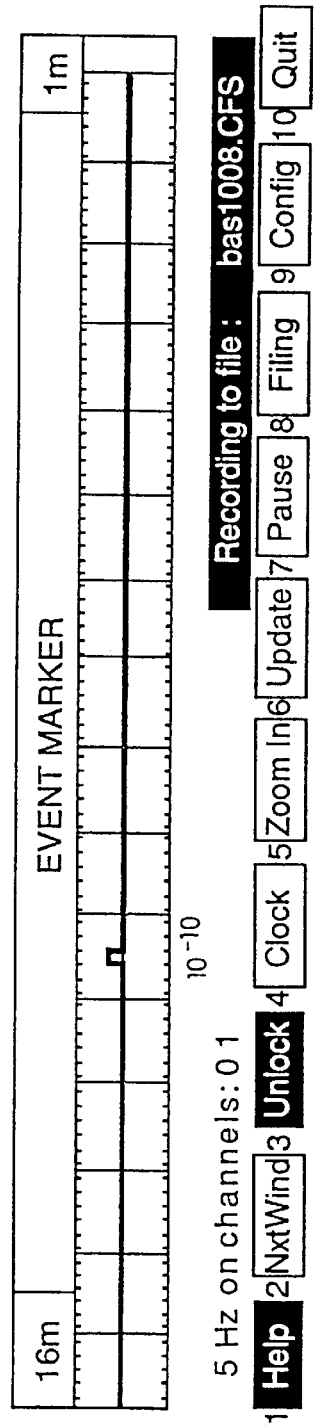
Figure 3B:
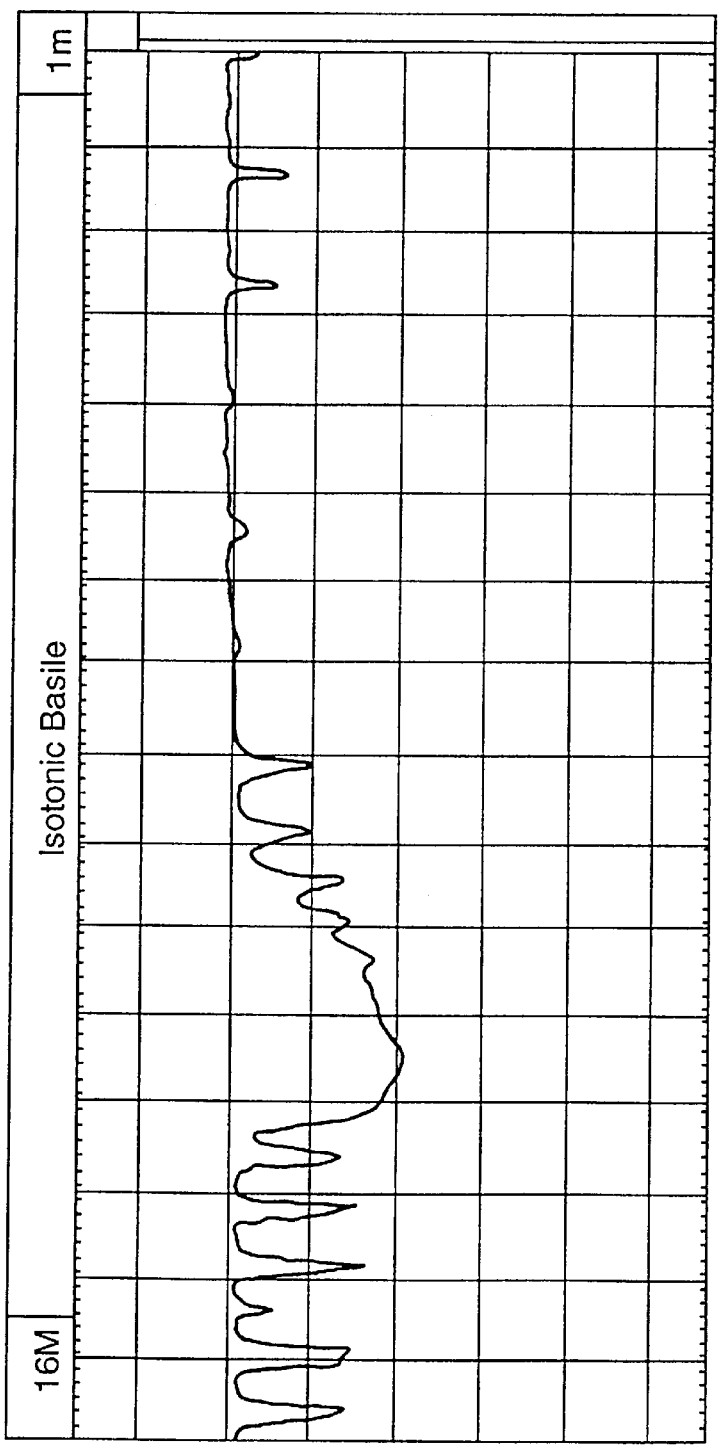
Figure 3B:
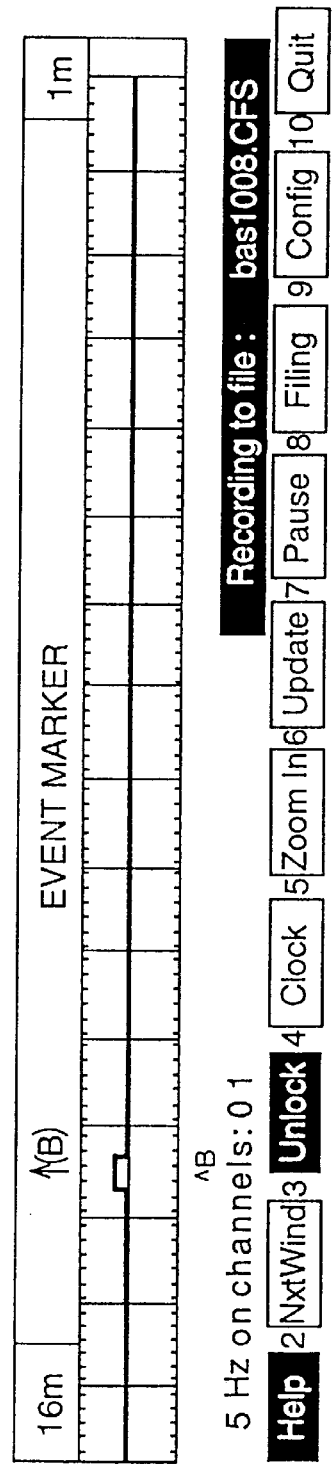

From FIG. 2(*a*) it can be seen that stimulation with angiotensin II significantly stimulated forward progressive velocity compared with the untreated controls, whilst addition of the monoclonal antibody inhibited the response to angiotensin II.

From FIG. 2(*b*) it can be seen that similar results were obtained for the effect on the percentage of motile sperm.

EXAMPLE 3

Effect of Monoclonal Antibody on Smooth Muscle Contractility in the Rat Uterus

The uterus was excised from a Wistar rat (350 g), and placed in minimum essential medium (MEM) and kept at room temperature. The organ was cleared of fat and a piece of tissue 3 cm long was cut from one horn and tied, using sutures, on to a basal isotonic transducer, which was linked to an analogue to digital converter. The resultant signal was analysed by computer using Chart software. A small weight (Approx. 1 g) was applied to take up tissue slack. The tissue was then totally immersed in incubation medium (MEM) in an isolated organ bath maintained at 37° C., and incubated until regular contractions of constant amplitude were observed. Fresh medium was applied and the tissue was once again allowed to equilibrate. The effects of angiotensin II, and monoclonal antibody on the rate and amplitude of contraction was assessed by adding these agents directly to the organ bath. The tissue was washed in several changes of medium between different test conditions.

From FIG. 3(*a*) it can be seen that, when angiotensin II at 0.1 nmole/l was added, at arrow (A), the amplitude and frequency of subsequent uterine contractions was significantly increased.

From FIG. 3(*b*) it can be seen that subsequent addition of monoclonal antibody, at arrow (B), inhibited the rate and intensity of the contractions to below, not only the angiotensin stimulated level, but also the basal level.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A hybridoma cell line which produces a monoclonal antibody capable of binding to the $AT_1$ subtype of the angiotensin II receptor and that binds specifically to amino acid residues 8–17 of the mammalian $AT_1$ receptor.

2. A hybridoma cell line according to claim 1 which produces a monoclonal antibody that binds specifically to amino acid residues 8–17 of rat vascular smooth muscle $AT_1$ receptor.

3. A hybridoma cell line which produces a monoclonal antibody that binds specifically to a peptide having the amino acid sequence (SEQ ID. No. 1)

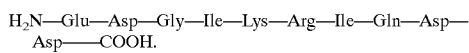

4. A hybridoma cell line which produces a monoclonal antibody capable of binding to the $AT_1$ subtype of the angiotensin II receptor, the cell line being characterized by cell line accession No. 930720117 deposited at European Collection of Animal Cell Cultures, Porton Down, UK.

5. A monoclonal antibody that binds to amino acid residues 8–17 of the mammalian $AT_1$ subtype of the angiotensin II receptor.

6. A monoclonal antibody according to claim 5 that binds specifically to amino acid residues 8–17 of rat vascular smooth muscle $AT_1$ receptor.

7. A monoclonal antibody according to claim 5 having a detectable label attached thereto.

8. A monoclonal antibody according to claim 7 wherein said label is a fluorescent label.

9. A monoclonal antibody according to claim 7 wherein said label is a radioisotope label.

10. A monoclonal antibody that binds specifically to a peptide having the amino acid sequence (SEQ ID. No. 1)

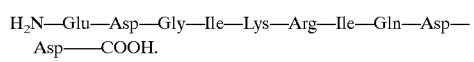

11. A monoclonal antibody that binds to the $AT_1$ subtype of the angiotensin II receptor, the antibody produced by a hybridoma cell line deposited at European Collection of Animal Cell Cultures, Porton Down, UK under accession No. 930720117.

* * * * *